United States Patent
Anklesaria

(10) Patent No.: US 7,808,392 B1
(45) Date of Patent: Oct. 5, 2010

(54) APPARATUS AND METHOD FOR MAGNET ATTACHMENT TO CLOTHING

(75) Inventor: Kaiomars P. Anklesaria, Bloomingdale, GA (US)

(73) Assignee: Enuresis Solutions LLC, Savannah, GA (US)

( * ) Notice: Subject to any disclaimer, the term of this patent is extended or adjusted under 35 U.S.C. 154(b) by 357 days.

(21) Appl. No.: 12/072,050

(22) Filed: Feb. 22, 2008

(51) Int. Cl.
*G08B 21/00* (2006.01)

(52) U.S. Cl. .................. 340/604; 340/605; 340/539.1; 340/573.5; 200/61.04; 200/61.05; 604/361

(58) Field of Classification Search .................. 340/604, 340/605, 539.1, 573.1, 573.5, 618; 128/205.23, 128/886; 200/61.04, 61.05; 604/131, 361
See application file for complete search history.

(56) References Cited

U.S. PATENT DOCUMENTS 4,356,479 A * 10/1982 Wilson .................. 340/604
5,459,452 A * 10/1995 DePonte .................. 340/573.5

* cited by examiner

*Primary Examiner*—Hung T. Nguyen
(74) *Attorney, Agent, or Firm*—G. Brian Pingel; Camille L. Urban

(57) ABSTRACT

The present invention provides an apparatus and method for removably attaching one or more electronic components to an article of clothing. Opposing magnets and attachment members for the magnets are placed on opposite sides of clothing.

17 Claims, 2 Drawing Sheets

APPARATUS AND METHOD FOR MAGNET ATTACHMENT TO CLOTHING

BACKGROUND OF THE INVENTION

1. Field of the Invention

The present invention relates in general to devices and method for attachment to clothing, and more specifically relates to a magnetic attachment to clothing.

2. Description of the Prior Art

It is known in the art to attach electronic sensors and other types of devices to clothing. One such example is in the field of enuresis detection and alarm systems. The prior devices and methods, however, are prone to damaging clothing when attached and removed. It is therefore for desirable to have an apparatus retained on clothing without damaging the clothing.

SUMMARY OF THE INVENTION

The present invention provides an apparatus for magnetic attachment to clothing. A first attachment member includes one or more magnets and a second attachment member includes one or more opposing magnets. The first attachment houses one or more electronic components and the magnets hold the electronic component to the clothing. One example of the present invention provided is magnetic attachment member of an enuresis detector/transmitting unit.

DETAILED DESCRIPTION OF PREFERRED EMBODIMENTS

Figure 1:
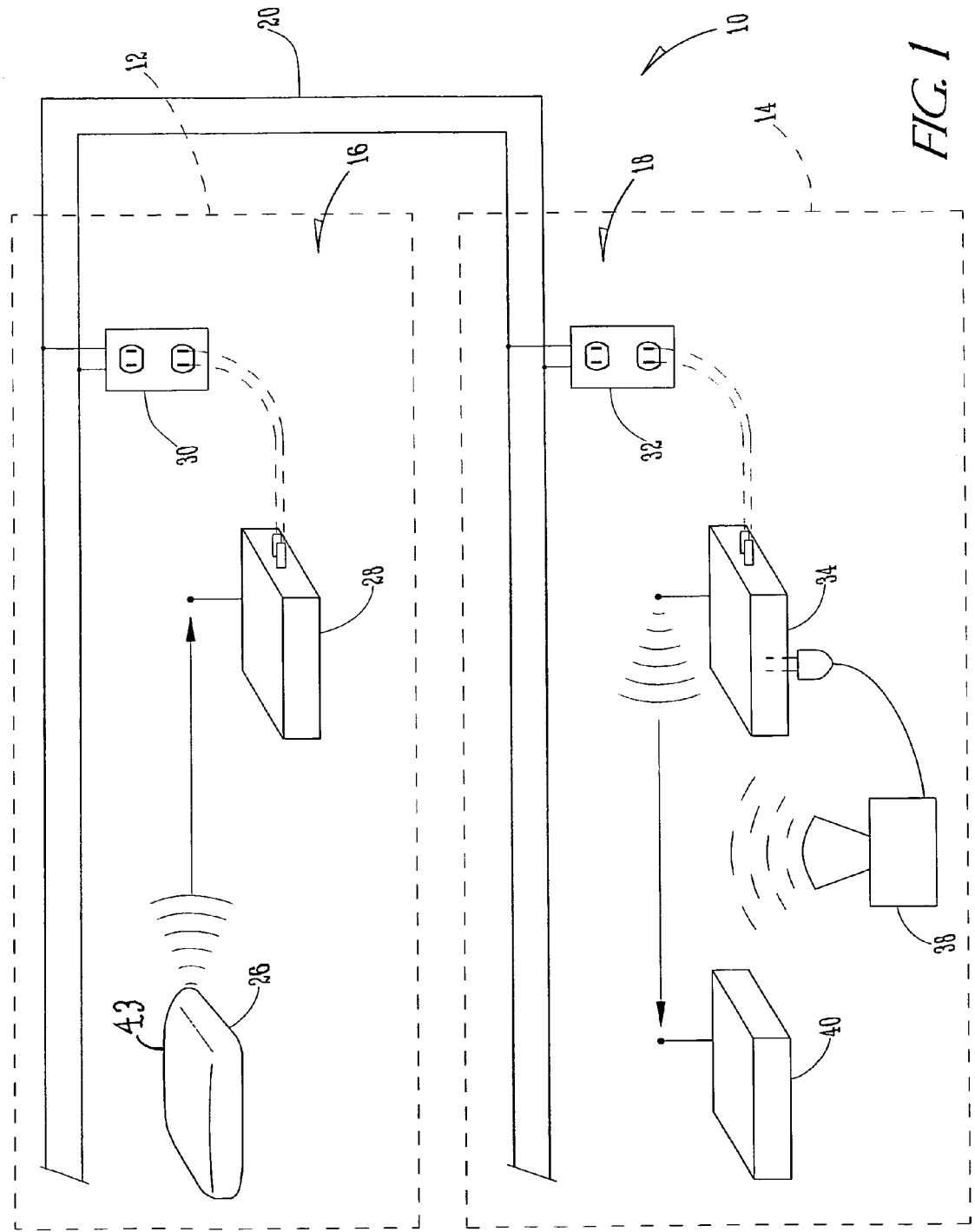
FIG. 1 is a diagrammatic illustration of a detection apparatus including a detector/transmitter unit.

FIG. 1 illustrates a detection and alarm apparatus 10 that is an example of an apparatus that is improved by the present invention. The detection and alarm apparatus 10 is designed for detecting urine in an article of clothing 11 a person (not shown) such as a child and providing an alarm signal to a caregiver (not shown) such as a parent. The detection and alarm apparatus 10 monitors the condition of the child in a room 12, indicated by dotted lines, and provide an alarm signal to a parent in a remote location represented by the dotted lines 14. The detection and alarm apparatus 10 incorporates a detecting and transmitting portion 16 located within the room 12 and a receiving and alarm portion 18 located in the remote location 14. Signals are transmitted between portions 16 and 18 via existing electrical wiring 20. Forming the detecting and transmitting portion 16 of the apparatus 10 is a detector/transmitter unit 26 and a transceiver 28 designed to be plugged into a normal electrical outlet 30. The detector/transmitter 26 may be battery operated so that it does not require any electrical wire connection to a source of power. Upon the detection of urine by the unit 26, it transmits a wireless sensing signal to the transceiver 28 that is plugged into the receptacle 30. The transceiver 28 is designed to receive the sensing signal from the detector/transmitter unit 26 and emit a powerline carrier electrical signal throughout such network including to an electrical outlet 32 located at the remote location 14 of the parent. The receiving and alarm portion 14 of the apparatus 10 includes a receiver unit 34 that is plugged into the outlet 32 and is actuated by transceiver 30 to close a switch providing power to an alarm device 38 that may produce an audible or visual alarm or both depending upon the preference of the parent. It is also possible to provide a wireless signal to a remote alarm device 40.

Although the detector/transmitter 26 and is preferably of small size so that it can readily be pinned to the article of clothing 11 or placed within a pocket, such means of attaching the detector/transmitter 26 to the article of clothing 11 are not desirable. Pinning has a tendency to damage the clothing 11 and the detector/transmitter has a tendency to fall out of pockets. The person wearing the clothing 11 is also likely to notice a pinned detector/transmitter 26 and may remove the detector/transmitter 26 out of discomfort, thus defeating the purposes of the detection and alarm apparatus 10.

Figure 2:
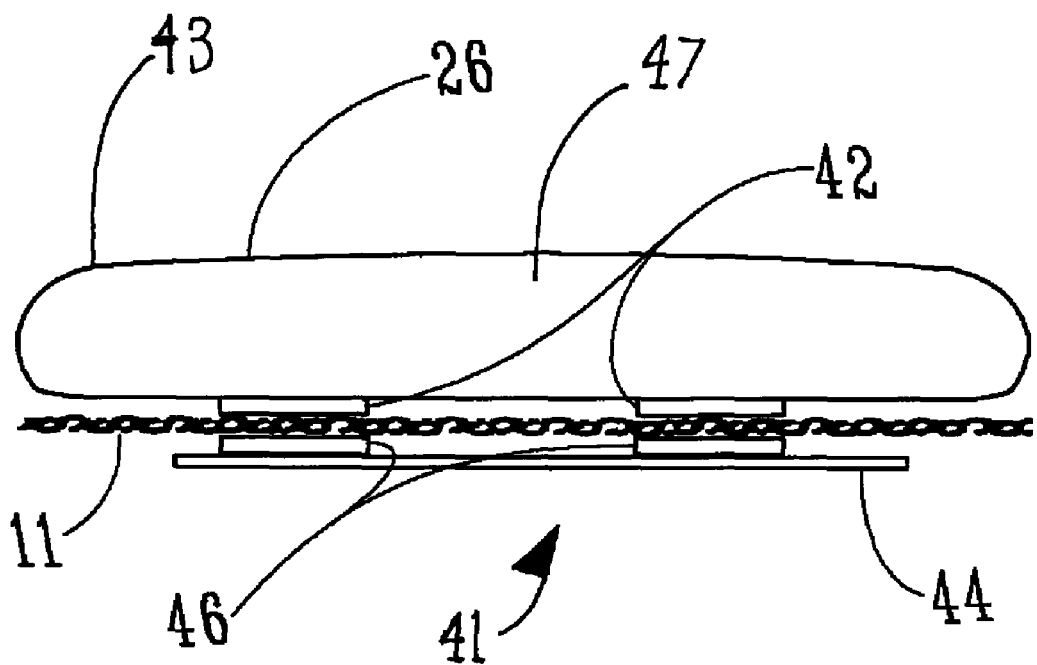
FIG. 2 is a front view in elevation of a first preferred embodiment of the present invention housing a detector/transmitter unit.

In a first preferred embodiment shown in FIG. 2, an apparatus 41 of the present invention includes magnets 42 attached to a first attachment member 43. A second attachment member 44 holds opposing magnets 46. The opposing magnets 46 are positioned on the second attachment member 44 to correspond to and engage the magnets 42 and hold the first attachment member 43 onto the clothing 11, shown as a cross section of cloth in FIG. 2. The first attachment member 43 houses at least one electronic component 47, such as for example, the detector/transmitter unit 26, and preferably also a battery (not shown). The electronic component 47 may be so formed as to serve as the first attachment member 43. The magnets 42 and 46 must necessarily be strong enough to hold the first attachment member 43 even when the article of clothing 11 is between the magnets. The magnets 42 and 46 are advantageous because they will not damage the article of clothing 11, as illustrated by the above example of an enuresis sensor.

Also, in the first preferred embodiment, the opposing magnets 46 project towards the first attachment member 43. It is preferable for this first preferred embodiment that the second attachment member 44 have a substantially smooth and flat surface to decrease the possibility that the person wearing the article of clothing 11 will notice attachment of the first attachment member 43 and dislodge it. In this manner, the first attachment member is more likely to remain on the article of clothing 26. The example of the enuresis sensor illustrates the advantages of the first embodiment.

Figure 3:
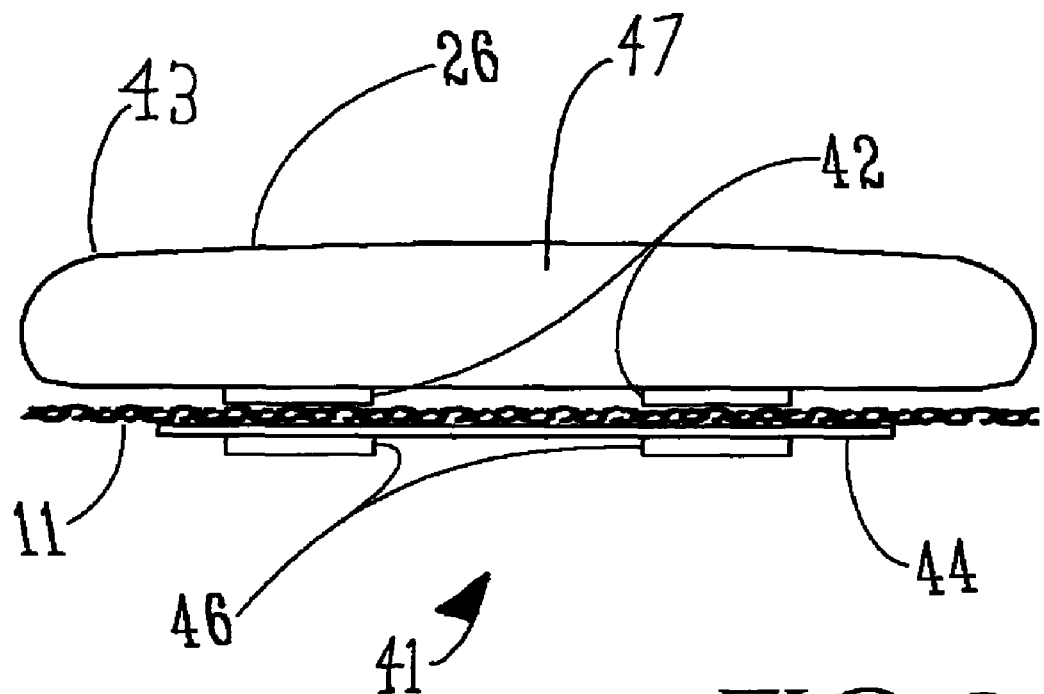
FIG. 3 is a front view in elevation of a second preferred embodiment of the present invention housing a detector/transmitter unit.

In a second preferred embodiment of the apparatus 41 shown in FIG. 3, the opposing magnets 46 project away from the second attachment member 44. It is also preferable for this second preferred embodiment that the second attachment member 44 have a substantially smooth and flat surface to decrease friction between the attachment member 44 and the article of cloth 11. Movement of the first attachment member 43 will therefore be less likely to cause disengagement of the magnets 42 and 46 as the second attachment member 44 is better able to slide along the clothing 11. In this manner, the first attachment member 43 is also more likely to remain on the clothing 11 in this second preferred embodiment. The example of the enuresis sensor again illustrates the advantages of this second preferred embodiment of the apparatus 41.

The present invention also encompasses the method as described herein for removably attaching the at least one electronic component 47 to the article of clothing 11. The at least one electronic component 47 must be attached to the at least one magnet 42 as described or by other means. The at least one electronic component 47 is positioned on the clothing 11 and at least one opposing magnet 46 is similarly positioned on opposite side of the clothing 11 such that the clothing 11 is between the magnets 42 and 46. The at least one opposing magnet 46 must be oriented such that it magnetically engages the at least one magnet 42 and removably retains the electronic component 47 onto the clothing 11. The method of the present invention can therefore be accomplished by either the first preferred embodiment or the second preferred embodiment of the apparatus 41.

The magnets 42 and 46 as described can be embedded into any object to hold the object onto a nonferrous or nonmagnetic material such as the article of clothing 11 or other fabric or paper materials. The magnets 42 and 46 are further useful for enuresis detection because the magnets 42 and 46 can serve as electrodes, and thus constitute a component of the detector/transmitter unit 26. Any moisture in the article of clothing 11 can be sensed through electrical current flowing between the magnets 42 and 46. Use of the magnets 42 and 46 are therefore advantageous in attaching objects to particular materials, avoiding damage to those materials, and aiding sensing of wetness in those materials.

Thus, the present invention has been described in an illustrative manner. It is to be understood that the terminology that has been used herein is intended to be in the nature of words of description rather than of limitation. Many modifications and variations of the present invention are possible in light of the above teachings. For example, although the example of an enuresis sensor is provided to illustrate the advantages of the present invention, the apparatus 41 is advantageous for attachment of any type of electronic component. Also, there can be a variety of methods for attachment of the magnets and indeed there can be any number of magnets attached. Therefore, within the scope of the appended claims, the present invention may be practiced otherwise than as specifically described.

What is claimed is:

1. An apparatus for removable attachment to an article of clothing, said apparatus comprising:
   a) at least one electronic component;
   b) a first attachment member housing said at least one electronic component and including at least one magnet;
   c) a second attachment member including at least one opposing magnet, said at least one opposing magnet oriented to magnetically engage said first attachment member; and
   d) said at least one magnet and said at least one opposing magnet sufficiently strong to removably retain said first attachment member and said second attachment member when said article of clothing is placed between said at least one magnet and said at least one opposing magnet.

2. An apparatus as recited in claim 1, wherein said at least one electronic component is a detector/transmitter for detecting the presence of urine and for transmitting a wireless sensing output signal in response thereto.

3. An apparatus as recited in claim 1, wherein said second attachment member attached is substantially smooth and flat for facilitating retention of said detector/transmitter unit on said article of clothing.

4. An apparatus as recited in claim 1, wherein said article of clothing is worn by a person and said second attachment member is substantially smooth and flat for decreasing the possibility that said person will notice association of said detector/transmitter unit with said article of clothing.

5. An apparatus as recited in claim 1, wherein said apparatus includes at least one battery, said first attachment means houses said at least one battery, and said at least one electronic component is battery operated.

6. An improvement to an apparatus for detecting the presence of urine in an article of clothing on a sufferer of enuresis located in one room of a building having an AC electrical wiring network with a plurality of wall outlets and providing in response an alarm signal to at least a location remote from such room, said apparatus comprising a detector/transmitter unit removably associated with said article of clothing for detecting the presence of urine and for transmitting a wireless sensing output signal in response thereto, a first means plugged into one of said wall outlets in said room for receiving said sensing signal and providing a transmission signal on the wiring of said electrical wiring network throughout said building, and a second means plugged into at least one of said wall outlets in said remote location for receiving said transmission signal and providing an alarm signal capable of immediately alerting a caregiver who is not actively providing care for said sufferer of enuresis in response thereto, said improvement comprising:
   a) a first attachment member housing said detector/transmitter unit and including at least one magnet;
   b) a second attachment member including at least one opposing magnet, said at least one opposing magnet oriented to magnetically engage said first attachment member; and
   c) said at least one magnet and said at least one opposing magnet sufficiently strong to removably retain said first attachment member and said second attachment member when said article of clothing is placed between said at least one magnet and said at least one opposing magnet.

7. An apparatus as recited in claim 6, wherein said at least one electronic component is a detector/transmitter for detecting the presence of urine and for transmitting a wireless sensing output signal in response thereto.

8. An apparatus as recited in claim 6, wherein said second attachment member attached is substantially smooth and flat for facilitating retention of said detector/transmitter unit on said article of clothing.

9. An apparatus as recited in claim 6, wherein said second attachment member is substantially smooth and flat for decreasing the possibility that said sufferer will notice association of said detector/transmitter unit with said article of clothing.

10. An apparatus as recited in claim 6, wherein said apparatus includes at least one battery, said first attachment means houses said at least one battery, and said at least one electronic component is battery operated.

11. A method for removably attaching at least one electronic component to an article of clothing, said method comprising:
    a) attaching to said at least one electronic component at least one magnet;
    b) positioning said at least one electronic component on said article of clothing;
    c) positioning on said clothing at least one opposing magnetic opposite said at least one magnet such that said clothing is between said at least one opposing magnet and said electronic component;
    d) orienting said at least one opposing magnet such that said at least one opposing magnet magnetically engages said at least one magnet to removably retain said at least one electronic component onto said article of clothing.

12. An apparatus as recited in claim 11, wherein said method includes the step of dressing a person in said article of clothing.

13. An apparatus as recited in claim 12, wherein said at least one electronic component is housed in a first attachment member and said at least one opposing magnet is attached to a second attachment member.

14. An apparatus as recited in claim 13, wherein said at least one electronic component is a detector/transmitter for detecting the presence of urine and for transmitting a wireless sensing output signal in response thereto.

15. An apparatus as recited in claim 13, wherein said second attachment member attached is substantially smooth and flat for facilitating retention of said detector/transmitter unit on said article of clothing.

16. An apparatus as recited in claim 13, wherein said second attachment member is substantially smooth and flat for decreasing the possibility that said person will notice association of said detector/transmitter unit with said article of clothing.

17. An apparatus as recited in claim 13, wherein said first attachment member houses at least one battery and said at least one electronic component is battery operated.

\* \* \* \* \*